United States Patent [19]

Lenzo

[11] Patent Number: 5,133,715
[45] Date of Patent: Jul. 28, 1992

[54] SURGICAL DEVICE FOR OPEN REDUCTION OF BONE FRACTURES

[76] Inventor: Salvatore R. Lenzo, 207 E. 16th St., New York, N.Y. 10003

[21] Appl. No.: 650,464

[22] Filed: Feb. 4, 1991

[51] Int. Cl.⁵ ............................................. A61F 5/04
[52] U.S. Cl. ........................................ 606/60; 606/53
[58] Field of Search ................ 606/53, 54, 57, 60, 606/86, 105

[56] References Cited

U.S. PATENT DOCUMENTS

| | | |
|---|---|---|
| 2,181,746 | 11/1939 | Siebrandt . |
| 2,200,120 | 5/1940 | Nauth . |
| 2,291,413 | 7/1942 | Siebrandt ............................ 606/86 |
| 2,427,128 | 9/1947 | Ettinger ............................. 606/86 |
| 2,460,470 | 2/1949 | Rogers . |
| 2,531,734 | 11/1950 | Hopkins . |
| 2,536,963 | 1/1951 | Stephens . |
| 2,583,896 | 1/1952 | Siebrandt . |
| 2,607,339 | 8/1952 | Price . |
| 3,477,429 | 11/1969 | Sampson . |
| 3,727,611 | 4/1973 | Jordan . |
| 3,835,849 | 9/1974 | McGuire . |
| 3,862,631 | 1/1975 | Austin ................................. 606/60 |
| 3,960,147 | 6/1976 | Murray ......................... 606/105 X |
| 4,096,857 | 6/1978 | Cramer et al. ..................... 606/57 |
| 4,257,411 | 3/1981 | Cho . |
| 4,349,017 | 9/1982 | Sayegh . |
| 4,360,012 | 11/1981 | McHarrie . |
| 4,364,381 | 12/1982 | Sher et al. . |
| 4,739,751 | 4/1988 | Sapega et al. . |
| 4,781,182 | 11/1988 | Purnell et al. . |

FOREIGN PATENT DOCUMENTS 581930  11/1977  U.S.S.R. .............................. 606/105

Primary Examiner—Robert A. Hafer
Assistant Examiner—Sam Rimell
Attorney, Agent, or Firm—Fitzpatrick, Cella, Harper & Scinto

[57] ABSTRACT

A device for use in open reduction of a bone fracture includes a first member for affixing to a first portion of a fractured bone; a second member for affixing to a second portion of the fractured bone separated from the first portion thereof as a result of the fracture; and a retaining element for retaining the first and second elements in a predetermined spaced relation such that the first and second portions of the fractured bone are thereby held together in their normal anatomical positions, the retaining element including a clamping device for clamping to at least one of the first and second elements for retaining the same in the predetermined spaced relation.

21 Claims, 2 Drawing Sheets

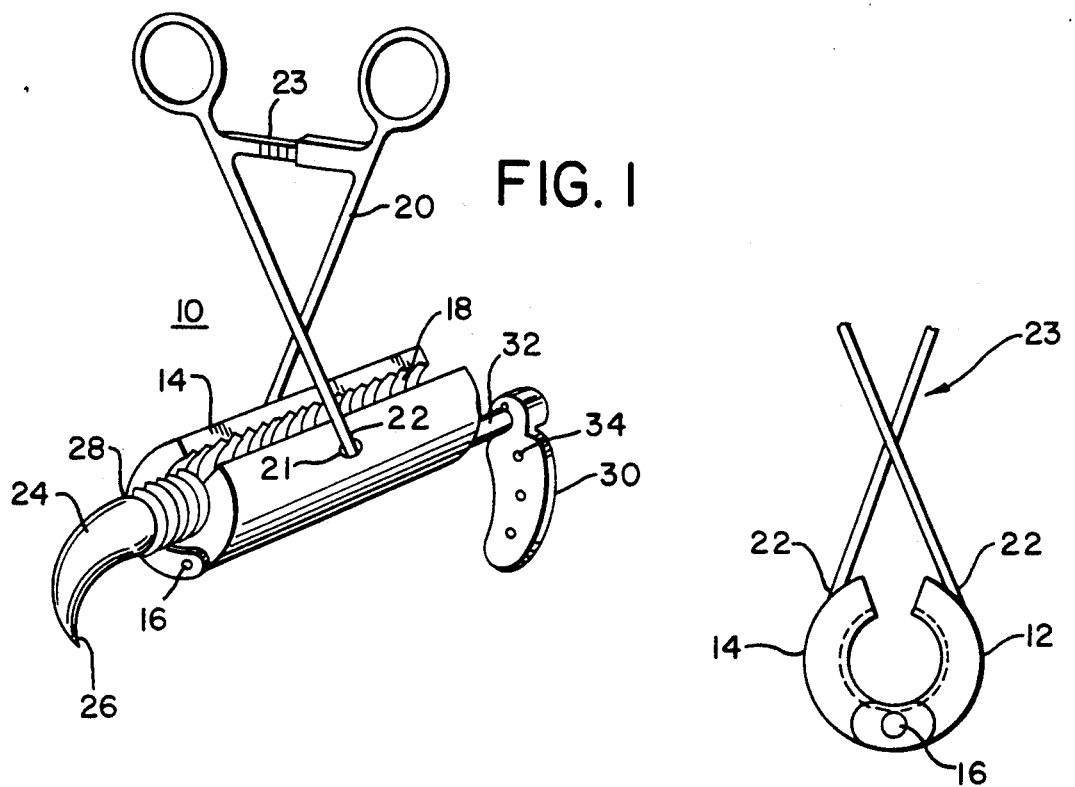
FIG. 1
FIG. 2
FIG. 3
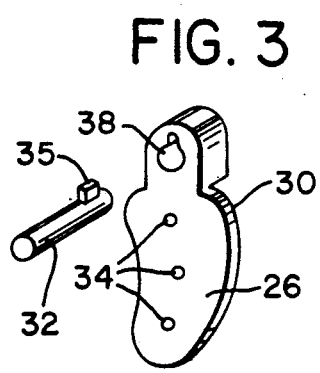
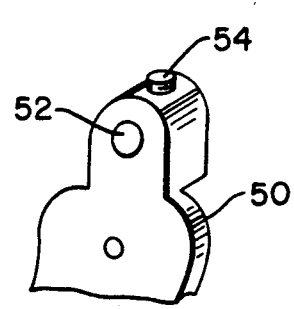
FIG. 5

SURGICAL DEVICE FOR OPEN REDUCTION OF BONE FRACTURES

BACKGROUND OF THE INVENTION

The present invention relates to devices for use in open reduction of bone fractures, and more particularly, to such a novel device which is readily adapted for miniaturization and which minimizes the potential for injury to articular cartilage and the like.

Open reduction is a surgical procedure for repositioning the separated portions of a fractured bone to permit them to heal in normal anatomical position. In this procedure, a device frequently is used for temporarily maintaining the separated portions of the bone in normal position while a permanent affixing device, such as a pin or a wire, is positioned in an aperture which the surgeon has formed through the broken portions of the bone with the use of a drill. Thereafter the temporary device is removed.

Conventional devices used in such surgical procedures for temporarily reducing bone fractures typically employ an affixing device having a pointed end for penetrating one of the broken portions of the bone in order to force it into proper position with the remaining portions thereof. The use of such devices for reducing a fracture of the articulated end of a bone causes injury to tissues such as articular cartilage, which in the future can result in an arthritic condition in the joint.

Such conventional devices also employ ratchets or screw-type devices to hold opposing ends of the device affixed to the bone fragments during the surgical procedure. Where it is necessary to reduce a fracture involving a small bone or a small portion of a bone, for example, in reducing the fracture of an articulated end of a bone in the hand or the foot, it is necessary that the devices employed in the procedure be miniaturized. However, devices which employ ratchets or screw-type mechanisms are poorly adapted for miniaturization.

SUMMARY AND OBJECTS OF THE INVENTION

Accordingly, it is an object of the present invention to provide a device for use in open reduction of a bone fracture which overcomes the disadvantages of conventional devices set forth above.

It is another object of the present invention to provide such a device which is easy to use.

It is a further object of the present invention to provide such a device for use in the open reduction of a fracture in the articular end of a bone while minimizing the likelihood of injury to adjacent tissues such as articular cartilage.

It is a still further object of the present invention to provide a device for use in open reduction of a bone fracture which is readily adapted for miniaturization for use in reducing small bone fractures.

In accordance with an aspect of the present invention, a device is provided for use in open reduction of a bone fracture, comprising first affixing means for affixing to a first portion of a fractured bone; second affixing means for affixing to a second portion of the fractured bone separated from the first portion thereof as a result of the fracture; and means for retaining the first and second affixing means in a predetermined spaced relation such that the first and second portions of the fractured bone are thereby held together in normal anatomical position, the retaining means comprising clamping means for clamping to at least one of the first and second affixing means for retaining the at least one of the first and second affixing means in the predetermined spaced relation. By providing a means for clamping to at least one of such first and second affixing means, the device of the present invention is readily adapted for miniaturization since the clamping means as well as the affixing means may be made desireably small. For example, either the first or the second affixing means may be a thin, elongated element which is easily retained in the predetermined spaced relation by clamping thereabout.

In accordance with a preferred embodiment of the present invention, one of the first and second affixing means comprises a member conforming generally to a surface of a portion of a fractured bone in order to urge it towards a further portion of the bone from which it has been separated for reestablishing a normal anatomical relationship thereof In this manner, the use of a sharp or pointed device which penetrates the bone, as well as adjacent tissue such as cartilage and the like, is avoided. This is especially advantageous where the articulated end of a fractured bone is repositioned pursuant to a reduction of the fracture, as the use of the present invention minimizes the injury to such adjacent tissues in order to avoid the development of an arthritic condition in the joint.

The above, and other objects, features and advantages of the invention, will be apparent in the following detailed description of certain illustrative embodiments thereof which is to be read in connection with the accompanying drawings forming a part hereof, and wherein corresponding parts and components are identified by the same reference numerals in the several views of the drawings.

BRIEF DESCRIPTION OF THE DRAWING

FIG. 1 is a partially enlarged, perspective view of a device in accordance with the present invention for use in the open reduction of a fracture of an articular end of a bone in a patient's hand;

FIG. 2 is a partial, elevational view of a longitudinal extremity of a hinged casing included in the device of FIG. 1;

FIG. 3 is a perspective view of one embodiment of a retaining plate included in the device of FIG. 1;

FIG. 5 is a partially broken away, perspective view of a second embodiment of a retaining plate included in the device of FIG. 1.

DESCRIPTION OF CERTAIN PREFERRED EMBODIMENTS

Figure 4:
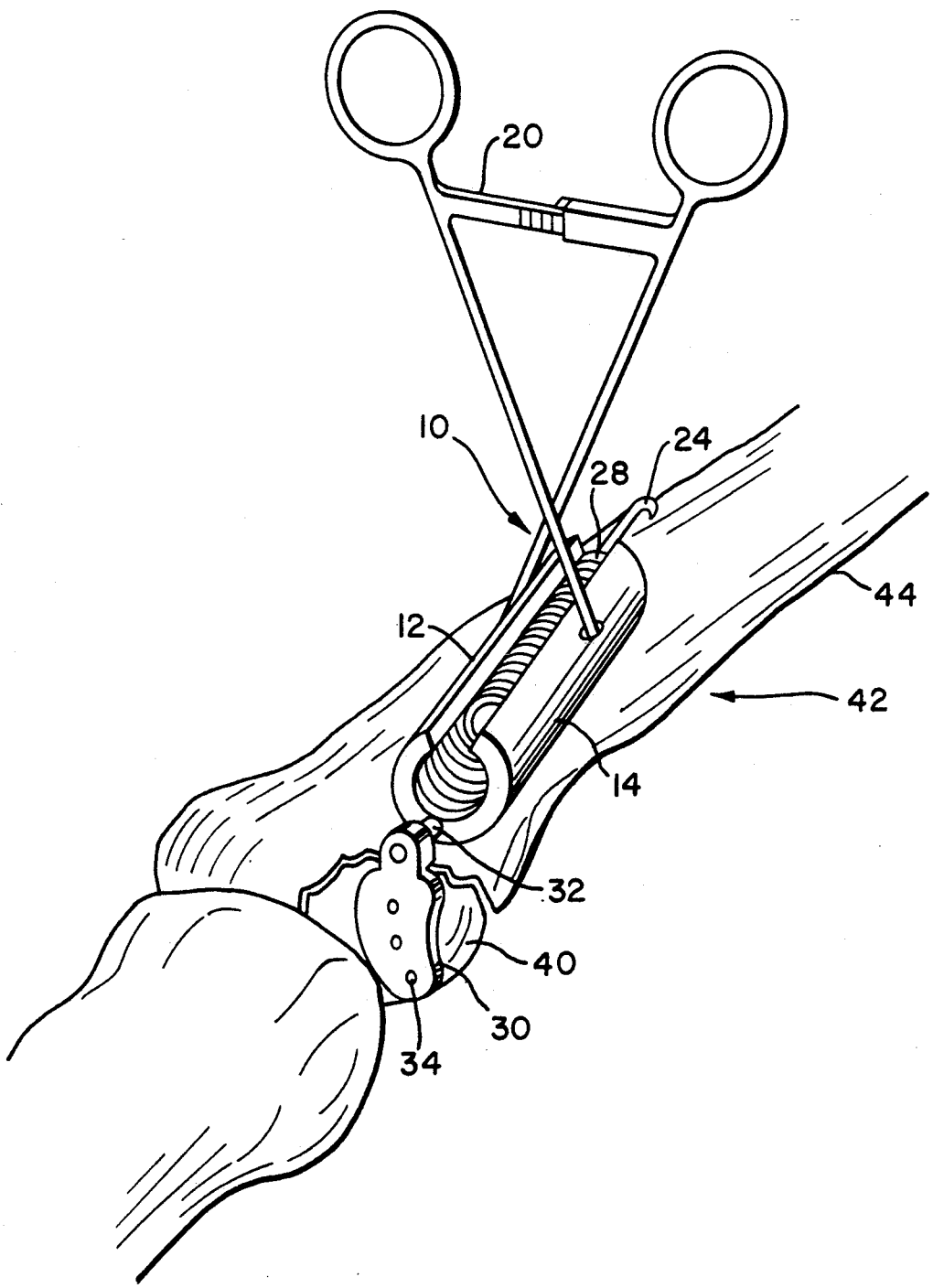
FIG. 4 is a partially enlarged, perspective view of the device of FIG. 1 in use to maintain a fractured portion of a broken knuckle in its normal anatomical position during the course of a surgical procedure for open reduction of the fracture.

Referring to the drawings in detail, and presently to FIG. 1 thereof, a device 10 for use in the open reduction of the articular end of a bone forming a knuckle of a patient's hand is illustrated therein. The device 10 includes a pair of clamping elements 12 and 14 each shaped generally as a semi-circular cylindrical section and pivotally joined adjacent a longitudinally extending edge surface thereof by a pivot pin 16 to form a hinged casing. With reference also to FIG. 2, the longitudinally extending edges of the respective clamping elements 12 and 14 may be provided with interdigitated projections having longitudinally aligned apertures for receiving the pivot pin 16 to pivotally mount the clamping elements 12 and 14 together. Each of the clamping elements 12 and 14 has a concave interior surface 18 facing the other thereof and formed as a plurality of circumferentially extending serrations.

A surgical clamp 20 is provided with distal ends 22 each of which is mated with a respective depression or aperture 21 in an outer surface of a corresponding one of the clamping elements 12 and 14 so that the elements 12 and 14 may be manually pivoted toward and away from one another, as desired, by means of the clamp 20. The clamp 20 is provided with a conventional ratchet mechanism 23 operative to releasably lock the distal ends 22 of the surgical clamp 20 as well as the clamping elements 12 and 14 in which the ends 22 are positioned.

Preferably, the surgical clamp 20 is a miniature version of a standard-size surgical clamp. It will be appreciated that an equivalent device may be provided to carry out the functions of the surgical clamp 20, and that a sufficiently small device may, in the alternative, be permanently affixed, as by welding, to the clamping elements 12 and 14.

A hooked member 24 is provided with a sharpened end portion 26 adapted to penetrate a surface of an unbroken portion of the fractured bone spaced from the articular end for affixing the device 10 to such unbroken portion. The hooked member 24 also includes a stem 28 having a generally elongated, cylindrical shape and having a plurality of circumferentially extending serrations on its surface which are sized and spaced so that they are complementary to the serrations 18 on the interior concave surfaces of the clamping elements 12 and 14, so that when the elements 12 and 14 are closed by means of the surgical clamp 20 to encompass the stem 28 of the hooked member 24, the hooked member 24 is fixed in position relative to the remainder of the device 10. It will be appreciated that the provision of a plurality of serrations on the interior concave surfaces of the clamping elements 12 and 14 complementary with a plurality of serrations on the surface of the stem 28 provides the ability to fix the hooked member 24 in any of a plurality of selectable, predetermined spaced relations with respect to the device 10.

A cylindrical stem 32 formed as an extension of the hinge pin 16 projects beyond the longitudinal extremities of the clamping elements 12 and 14 opposite the extremities thereof from which the hooked member 24 projects. With reference also to FIG. 3, a retaining plate 30 has an interior surface 36 shaped generally to conform with the exterior surface of an articular end of the finger bone which has been separated from the remainder thereof as a result of a fracture. The retaining plate 30 also includes a keyed aperture 38 therethrough of a size and shape to permit a key 35 formed as a radial projection on the longitudinal extremity of the stem 32 to be inserted through the aperture 38 in the retaining plate 30, which is then rotated on the stem 32 so that it is releasably retained thereon. The retaining plate 30 is provided with a plurality of guideholes 34 extending from the interior surface 36 of the retaining plate 30 to an opposite, exterior surface thereof.

With reference now to FIG. 4, the device 10 is illustrated therein in use during the course of an open reduction of a broken knuckle in a patient's hand. In FIG. 4, a bone fragment 40 forming a portion of an articular end of a finger bone 42 is shown held in its normal anatomical position by means of the device 10.

In use, the hooked member 24 is pressed into an unbroken portion 44 of the one 42 spaced from the articular end and the bone fragment 40 thereof so that the hooked member 24 is anchored therein. Then an appropriately sized retaining plate 30 is slid over the keyed, distal end of the cylindrical stem 32 and rotated so that it is held thereon, and then positioned against the outer surface of the bone fragment 40 as it is positioned in normal anatomical relationship with respect to the unbroken portion 44. As the retaining plate 30 is thus held against the bone fragment 40 and while the hooked member 24 is anchored in the unbroken portion 44 as described above, the surgical clamp 20 is closed manually so that the clamping elements 12 and 14 encompass the stem 28 of the hooked member 24 thus to clamp transversely thereabout to retain the same in a fixed position relative to the device 10. The retaining plate 30 is thus firmly held against the bone fragment 40 as the plate 30 exerts pressure through the pivot pin 16 and the clamping elements 12 and 14 against the hooked member 24 while the same is anchored in the unbroken portion 44 of the bone 42, thus to maintain the bone fragment 40 in its normal anatomical position for the remainder of the surgical procedure.

The surgeon then drills a hole through one of the guideholes 34 into the bone fragment 40 and therefrom into the unbroken portion 44 of the bone 42. Thereafter, an appropriate wire or pin is passed through the corresponding one of the guideholes 34 through the bone fragment 40 and into the unbroken portion 44 to permanently fasten the fragment 40 to the portion 44. Once this is accomplished, the surgical clamp 20 is manipulated by the surgeon to open the clamping elements 12 and 14 thus to permit the hooked member 24 to move longitudinally with respect thereto so that the retaining plate 30 and the hooked member 24 may be removed from the patient's hand.

With reference now to FIG. 5, an alternative embodiment 50 of the retaining plate 30 is illustrated therein having a cylindrical aperture 52 therethrough for receiving an unkeyed distal end of a modified stem of the pivot pin 16. A set screw 54 is seated in a threaded aperture of the retaining plate 50 disposed transverse to the cylindrical aperture 52 and extending thereto so that the set screw 54 may be rotated downwardly into the cylindrical aperture 52 to engage and releasably affix the retaining plate 50 to the modified stem of the pivot pin 16.

Although specific embodiments of the invention have been described in detail herein with reference to the accompanying drawings, it is to be understood that the invention is not limited to those precise embodiments. For example, the casing may have any of a number of different configurations, such as rectangular, square, oval, "V" shaped, etc. It will be appreciated, therefore, that various changes and modifications may be effected in the specific embodiments of the invention disclosed herein by one skilled in the art without departing from the scope or spirit of the invention as defined in the amended claims.

I claim:

1. A device for use in open reduction of a bone fracture, comprising:
   first affixing means for affixing to a first portion of a fractured bone;

second affixing means for affixing to a second portion of the fractured bone separated from the first portion thereof as a result of the fracture; and clamping means for retaining said first and second means in a predetermined spaced relation such that the first and second portions of the fractured bone are thereby held together in normal anatomical position; one of said first and second affixing means being mounted in a fixed position on the clamping means and the other of the affixing means including an elongated stem movable in the clamping means relative to the fixed affixing means;

said clamping means including means for applying a clamping force to the stem of said other affixing means, transversely of its longitudinal axis for retaining said other of said first and second affixing means in a fixed position thereby to define said predetermined spaced relation.

2. The device according to claim 1, wherein said second affixing means comprises means for affixing to a separated portion of said fractured bone normally forming an articular end thereof in an unfractured condition.

3. The device according to claim 1, wherein said first means comprises a hooked member having a pointed tip for penetrating a surface of the first portion of the fractured bone to affix said first means thereto.

4. The device according to claim 3 wherein said hooked member is elongated and said means for clamping comprises means for clamping transversely about the elongated member.

5. The device according to claim 1, wherein said second affixing means comprises a member conforming generally to a surface of the second portion of the fractured bone normally facing away from the first portion thereof in an unfractured condition for abutting the surface of the second portion to urge the second portion into a normal anatomical relationship with the first portion.

6. The device according to claim 1, wherein said clamping means includes a hinged casing operative to encompass at least a portion of said at least one of said first and second affixing means.

7. The device according to claim 1, wherein said clamping means includes means for encompassing at least a portion of said at least one of said first and second affixing means.

8. The device according to claim 7, wherein said clamping means further includes manually actuatable means for operating said means for encompassing such that said means for encompassing is releasably engaged with said at least one of said first and second affixing means.

9. The device according to claim 7, wherein said manually actuatable means comprises a surgical-type clamp.

10. A device for use in open reduction of a bone fracture, comprising:

first affixing means for affixing to a first portion of a fractured bone;

second affixing means for affixing to a second portion of the fractured bone separated from the first portion thereof as a result of the fracture; and clamping means for retaining said first and second means in a predetermined spaced relation such that the first and second portions of the fractured bone are thereby held together in normal anatomical position;

said second affixing means comprising means for affixing to a separated portion of said fractured bone normally forming an articular end thereof in an unfractured condition;

said first affixing means comprising a hooked member having a pointed tip for penetrating a surface of the first portion of the fractured bone to affix said first means thereto; said hooked member being elongated and said clamping means clamping transversely about the elongated member; and each of said elongated hook member and said clamping means being provided with a serrated surface positioned to face the other thereof in clinical use such that the serrated surface of said clamping means is operative to mate with the serrated surface of said elongated hook member to maintain said first and second means in one of a plurality of selectable predetermined spaced relations.

11. A device for use in open reduction of a bone fracture, comprising:

first affixing means for affixing to a first portion of a fractured bone;

second affixing means for affixing to a second portion of the fractured bone separated from the first portion thereof as a result of the fracture; and clamping means for retaining said first and second means in a predetermined spaced relation such that the first and second portions of the fractured bone are thereby held together in normal anatomical position;

said second affixing means comprising a member conforming generally to a surface of the second portion of the fractured bone normally facing away from the first portion thereof in an unfractured condition for abutting the surface of the second portion to urge the second portion into a normal anatomical relationship with the first portion;

and said member of said second affixing means being formed with at least one aperture extending therethrough and positioned such that a permanent affixing device may be introduced through said member to extend from the second portion of the fractured bone into the first portion thereof.

12. The device according to claim 11, wherein the member of said second affixing means conforms generally to a surface of an articular end of the fractured bone separated from a remaining portion thereof for abutting the surface of the articular end to urge the articular end into normal anatomical relationship therewith.

13. A device for use in open reduction of a bone fracture, comprising:

first affixing means for affixing to a first portion of a fractured bone;

second affixing means for affixing to a second portion of the fractured bone separated from the first portion thereof as a result of the fracture; and clamping means for retaining said first and second means in a predetermined spaced relation such that the first and second portions of the fractured bone are thereby held together in normal anatomical position;

said second affixing means comprising a member conforming generally to a surface of the second portion of the fractured bone normally facing away from the first portion thereof in an unfractured condition for abutting the surface of the second portion to urge the second portion into a normal anatomical relationship with the first portion;

said member of said second affixing means being operative to be removably fastened to said retaining means.

14. The device according to claim 13, wherein the member of said second affixing means is formed with a keyed aperture and said retaining means is provided with a key conforming with the keyed aperture of said member of said second affixing means for mating therewith to removably fasten said retaining means to said member of said second means.

15. The device according to claim 13, wherein said member of said second affixing means is formed with an aperture and said retaining means is provided with a projection configured to fit within the aperture of said member, said member being further provided with a set screw extending transversely into the aperture thereof to retain said projection therein for removably fastening said member of said second affixing means to said retaining means.

16. A device for use in open reduction of a bone fracture, comprising:

first affixing means for affixing to a first portion of a fractured bone;

second affixing means for affixing to a second portion of the fractured bone separated from the first portion thereof as a result of the fracture; and clamping means for retaining said first and second means in a predetermined spaced relation such that the first and second portions of the fractured bone are thereby held together in normal anatomical position;

said clamping means including a hinged casing operative to encompass at least a portion of said at least one of said first and second affixing means;

said hinged casing including first and second elongated portions and hinge means for joining said first and second elongated portions in pivoting relationship along respective longitudinally extending edges thereof, said elongated portions having respective concave inner surfaces in mutually facing relation.

17. The device according to claim 16, wherein said hinge means comprises an elongated pin extending beyond longitudinal extremities of said first and second elongated portions, said retaining means further comprising means for releasably securing the other of said first and second affixing means to said retaining means.

18. The device according to claim 17, wherein said means for releasably securing the other of said first and second affixing means comprises a key and said other of said first and second affixing means is formed with an aperture configured to mate with said key to removably affix said elongated pin to said other of said first and second affixing means.

19. The device according to claim 17, wherein said means for releasably securing the other of said first and second affixing means comprises a set screw disposed in said other of said first and second affixing means transversely to a surface of an aperture therein arranged to receive said elongated pin for exerting transverse pressure thereagainst to releasably retain said elongated pin in said aperture.

20. The device according to claim 16, wherein said at least one of said first and second affixing means comprises an elongated shaft and said means for clamping is operative to encompass said elongated shaft to clamp thereto.

21. The device according to claim 16, wherein said respective concave inner surfaces are provided with serrations for gripping said at least one of said first and second affixing means.

* * * * *